United States Patent [19]

Irikura et al.

[11] Patent Number: 4,680,398

[45] Date of Patent: Jul. 14, 1987

[54] PYRAZOLO[1,5-A]PYRIDINES AND BENZIMIDAZOLES, USEFUL AS ANTIALLERGIC AGENTS

[75] Inventors: Tsutomu Irikura, Tokyo; Keigo Nishino, Oomiya; Kyuya Okamura, Oomiya; Toshiya Ikeda, Oomiya, all of Japan

[73] Assignee: Kyorin Pharmaceutical Co., Ltd., Tokyo, Japan

[21] Appl. No.: 824,099

[22] Filed: Jan. 30, 1986

[30] Foreign Application Priority Data

Feb. 14, 1985 [JP] Japan ................... 60-27267

[51] Int. Cl.$^4$ .................. C07D 471/04; C07D 235/28
[52] U.S. Cl. ..................... 546/121; 548/329

[58] Field of Search ............... 546/121; 514/300, 395; 548/329

[56] References Cited

FOREIGN PATENT DOCUMENTS 0149585 8/1985 Japan ................... 546/121

OTHER PUBLICATIONS

Morrison et al., Org. Chem. 3rd Ed. pp. 555–557.
Morrison & Boyd Org. Chem. pp. 822–831.

*Primary Examiner*—John M. Ford
*Assistant Examiner*—J. Richter
*Attorney, Agent, or Firm*—Oblon, Fisher, Spivak, McClelland & Maier

[57] ABSTRACT

The present invention is concerned with certain novel anti-allergic agents and process for their preparation.

10 Claims, No Drawings

PYRAZOLO[1,5-A]PYRIDINES AND BENZIMIDAZOLES, USEFUL AS ANTIALLERGIC AGENTS

DETAILED DESCRIPTION OF THE INVENTION

The present invention is concerned with novel compounds having an antiallergic activity and their manufacturing methods.

Certain types of cells, for example, mast cells release the chemical mediators which mediate the allergic reaction in response to antigen-antibody reactions. As the chemical mediators participating in the immediate allergic reaction, histamines and SRS-A (slow reacting substance of anaphylaxis) are looked upon as important, but the latter plays the most important role particularly in bronchial asthma. SRS-A is the mixture of leukotriene $C_4$ ($LTC_4$), leukotriene $D_4$ ($LTD_4$) and leukotriene $E_4$ ($LTE_4$), which are metabolites of arachidonic acid by 5-lipoxygenase pathway. In general, the study of the medicinal drugs to prevent, improve and remove the symptoms of allergic reaction has been directed to the development of those inhibit the release of chemical mediator or antagonize to the action of it. As a result, antihistaminics (for example, diphenhydramine, chloropheniramine, etc.), SRS-A release inhibitors (disodium cromoglycate) and the like are on the market. However, the effect of the former against bronchial asthma is unreliable, and the latter has the only preventive activity and has no effects when used internally.

Therefore, the drugs which antagonize the action of SRS-A are expected to be useful as antiallergic agents. At this time, only a few drugs are known to have such an activity, but none of them are known to have such an activity when used internally.

As a result of the sensitive investigation on the compounds having an antiallergic action, the present inventors have found that novel compounds shown by a formula (I) have an excellent antiallergic action, in particular, extremely powerful inhibitory action on the anaphylaxis, which may be caused by SRS-A, even when used internally.

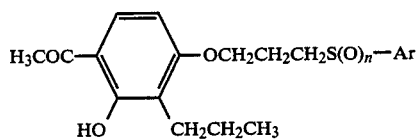
(I)

wherein Ar stands for a pyrazolo [1,5-a]pyridin-3-yl ring with or without a substituent like a straight or branched alkyl group having 1 to 4 carbon atoms or for a benzimidazol-2-yl group, and n means an integer of 0 to 2.

According to the present invention, the compounds shown by the general formula (I) can be manufactured through various pathways.

(1) The compounds wherein n means 0 in a general formula (I) can be manufactured through allowing the compounds of a general formula (II) to react with phenoxyalkyl derivatives of a general formula (III). Typically, they can be manufactured through allowing the compounds of a general formula (II) to react with phenoxyalkyl derivatives of a general formula (III) in a suitable solvent, for example, methanol, ethanol, tetrahydrofuran or the like, and in the presence or absence of the base, for example, potassium hydroxide, sodium hydride or the like.

$$Ar-SH \quad (II)$$

wherein Ar is same as described above.

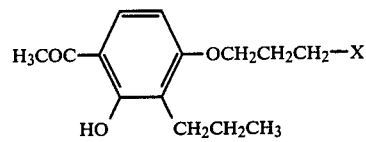
(III)

wherein X is halogen atom.

(2) The compounds wherein n means 0 in the general formula (I) can also be manufactured after converting the compounds of a general formula (IV) to the compounds of a general formula (II), which are then reacted with the compounds of a general formula (III) by the same method as (1). Typically, the compounds of a general formula (IV) are converted to the compounds of a general formula (II) by a suitable reagent, for example, zinc-hydrochloric acid, sodium borohydride, potassium hydroxide or the like, in a suitable solvent, for example, methanol, ethanol or the like.

$$Ar-SCN \quad (IV)$$

wherein Ar stands for same as described above.

(3) The compounds wherein n means 1 in a general formula (I) can be manufactured through allowing the compounds wherein n means 0 in a general formula (I) to react with oxidizing reagents. Typically, they can be manufactured through allowing the compounds wherein n means 0 in a general formula (I) to react with one or more molar equivalents mild oxidizing reagents, for example, hydrogen peroxide in methanol, m-chloroperbenzoic acid in dichloromethane or the like.

(4) The compounds wherein n means 2 in a general formula (I) can also be manufactured through allowing the compounds wherein n means 0 in a general formula (I) to react with oxidizing reagents in the same manner as (3). Typically, they can be manufactured through allowing the compounds wherein n means 0 in a general formula (I) to react with two or more molar equivalents mild oxidizing reagents in the same manner as (3).

In following, the present invention will be explained by using concrete examples. But the invention is not confined to them.

REFERENTIAL EXAMPLE 1

Manufacture of 2-isopropyl-3-thiocyanopyrazolo[1,5-a]pyridine

To a solution of 3 g of 2-isopropylpyrazolo[1,5-a]pyridine in 56 ml of methanol was added 5.74 g of potassium thiocyanate and stirred at room temperature. 3.3 g of bromine was dissolved in 13 ml of methanol saturated with potassium bromide and added dropwise to the previous solution. Then, the mixture was stirred at room temperature for an hour, poured into 130 ml of water and resulting precipitate was filtered and dried. This crude precipitate was recrystallized from methanol to give 3.53 g (yield 87%) of the aimed compound as pale yellow prismatic crystals. mp 91°–92.5° C.

REFERENTIAL EXAMPLE 2

Manufacture of 2-methyl-3-thiocyanopyrazolo[1,5-a]pyridine

This compound was synthesized by the same method as referential example 1 using 2-methylpyrazolo[1,5-a]pyridine instead of 2-isopropylpyrazolo[1,5-a]pyridine. Pale yellow powder (yield 50%). mp 111°–113° C.

EXAMPLE 1

Manufacture of 2-[3-(4-acetyl-3-hydroxy-2-propylphenoxy)propylthio]-benzimidazole To a suspension of 1.2 g of 2-mercaptobenzimidazole in 30 ml of ethanol was added 580 mg of potassium hydroxide under stirring and stirred at room termperature for 10 minutes. To this solution was added 2.8 g of 3-(4-acetyl-3-hydroxy-2-propylphenoxy)propylbromide at one time, and stirred at room temperature for 4 hours. The solvent was distilled off under reduced pressure and resulting residue was diluted with dichloromethane-water, then extracted with dichloromethane three times. The organic layer was combined, then washed with water saturated with sodium chloride and dried over anhydrous sodium sulfate. The solvent was distilled off under reduced pressure, the resulting residue was recrystallized from dichloromethane-n-hexane to give 2.5 g (yield 81%) of the aimed compound as colorless powder. mp 149°–150° C.

Analysis (%) for $C_{21}H_{24}N_2O_3S$: Calcd. (Found); C, 65.60 (65.71); 6.29 (6.29); N, 7.29 (7.24).

EXAMPLE 2

Manufacture of 3-[3-(4-acetyl-3-hydroxy-2-propylphenoxy)propylthio]-2-isopropylpyrazolo[1,5-a]pyridine To a suspension of 1 g of 2-isopropyl-3-thiocyanopyrazolo[1,5-pyridine (described in referential example 1) in 25 ml of methanol was added 2.6 ml of concentrated hydrochloric acid and stirred at room temperature. To this solution was added 1.3 g of zinc powder little by little, then stirred at room temperature for an hour. This solution was diluted with 40 ml of water and extracted with dichloromethane twice, then organic layer was combined, dried over anhydrous sodium sulfate and the solvent was distilled off under reduced pressure. The resulting residue was reacted with the same method as example 1, the crude products were purified by flash column chromatography (dichloromethane:benzene=2:1) and then recrystallized from n-hexane to give 750 mg (yield 38%) of the aimed compound as colorless needles. mp 95°–95.5° C.

Analysis (%) for $C_{24}H_{30}N_2O_3S$: Calcd. (Found); C, 67.58 (67.70); H, 7.09 (7.19); N, 6.57 (6.43).

EXAMPLE 3

Manufacture of 3-[3-(4-acetyl-3hydroxy-2-propylphenoxy)propylthio]-2-isopropylpyrazolo[1,5-a]pyridine-S-oxide To a solution of 800 mg of 3-[3-(4-acetyl-3-hydroxy-2-propylphenoxy)propylthio]-2-isopropylpyrazolo[1,5-a]pyridine (described in example 2) in 25 ml of dichloromethane, cooled with ice-salt-water bath below 0° C., was added 405 mg of m-chloroperbenzoic acid and stirred at 0° C. for 15 minutes. To the reacting mixture was added 4 g of calcium hydroxide and stirred at room temperature for 10 minutes, the precipitate of suspension was filtered off with Celite. The filtrate was further washed with 5% aqueous sodium hydrogencarbonate solution, dried over anhydrous sodium sulfate and the solvent was distilled off under reduced pressure. The crystalline residue was recrystallized from dichloromethane-n-hexane to give 770 mg (yield 93%) of the aimed compound as colorless powder. mp 145°–146° C.

Analysis (%) for $C_{24}H_{30}N_2O_4S$: Calcd. (Found); C, 65.13 (65.17); H, 6.83 (6.79); N, 6.33 (6.23).

EXAMPLE 4

Manufacture of 3-[3-(4-acetyl-3-hydroxy-2-propylphenoxy)propylsulfonyl]-2-isopropylpyrazolo[1,5-a]pyridine To a solution of 2 g of 3-[3-(4-acetyl-3-hydroxy-2-propylphenoxy)propylthio]-2-isopropylpyrazolo[1,5-a]pyridine (described in example 2) in 50 ml of dichloromethane, cooled with water bath below 15° C., was added 2.22 g of m-chloroperbenzoic acid and stirred at room temperature for 2 hours. The purification procedure was same as described in example 3. The resulting residue was further recrystallized from dichloromethane-n-hexane to give 1.98 g (yield 92%) of the aimed compound as pale yellow powder. mp 169.5°–170.5° C.

Analysis (%) for $C_{24}H_{30}N_2O_5S$: Calcd. (Found); C, 62.86 (62.70); H, 6.59 (6.66); N, 6.11 (6.01).

Using the procedure described in examples 1 to 4, compounds shown in Table 1 were synthesized.

TABLE 1

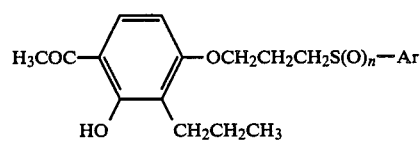

(I)

| Example No. | Manufacture method (example No.) | Ar | n | yield (%) | mp (°C.) | Analysis (%) Calcd. Found C | H | N |
|---|---|---|---|---|---|---|---|---|
| 5 | 2 | 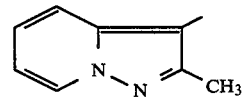 | 0 | 27 | 96–98 | for $C_{22}H_{26}N_2O_3S$ 66.31 66.34 | 6.58 6.46 | 7.03 6.89 |

TABLE 1-continued $$H_3COC-\text{[benzene ring]}-OCH_2CH_2CH_2S(O)_n-Ar \quad (I)$$

with HO and $CH_2CH_2CH_3$ substituents

| Example No. | Manufacture method (example No.) | Ar | n | yield (%) | mp (°C.) | Analysis (%) Calcd. Found C | H | N |
|---|---|---|---|---|---|---|---|---|
| 6 | 3 | 3-methyl-pyrazolo[1,5-a]pyridin-2-yl | 1 | 76 | 109–111 | for $C_{22}H_{26}N_2O_4S$ 63.75 63.61 | 6.32 6.34 | 6.76 6.71 |
| 7 | 4 | 3-methyl-pyrazolo[1,5-a]pyridin-2-yl | 2 | 77 | 141–142 | for $C_{22}H_{26}N_2O_5S$ 61.38 61.21 | 6.09 6.12 | 6.51 6.43 |
| 8 | 3 | benzimidazol-2-yl | 1 | 60 | 172–173 | for $C_{21}H_{24}N_2O_4S$ 62.98 62.89 | 6.04 6.02 | 6.99 7.08 |
| 9 | 4 | benzimidazol-2-yl | 2 | 43 | 179–180 | for $C_{21}H_{24}N_2O_5S$ 60.56 60.36 | 5.81 5.83 | 6.72 6.78 |

The compounds presented here have shown a potent antagonizing effect on $LTD_4$-induced contraction of the isolated guinea-pig ileum. Noticeably, all the compounds are orally effective in the experimental model of bronchial asthma. Inhalation of aerosolized antigen to actively sensitized guinea-pigs treated beforehand with indomethacin and tripelennamine induces anaphylactic bronchoconstriction, in which endogenously released SRS-A may play a predominant role. The compounds of the present invention strongly inhibited this anaphylactic bronchoconstriction at the oral dose of 20 mg/kg (Table 2). FPL55712, sodium 7-[3-(4-acetyl-3-hydroxy-2-propylphenoxy)-2-hydroxypropoxy]-4-oxo-8-propyl-4H-1-benzopyran-2-carboxylate, a well known SRS-A antagonist, is reported to be orally inactive (P. Sheard et al.: Monogr. Allergy, pp. 244–248. S. Karger, 1977). Thus, the compounds of the present invention are promising antiallergic agents possessing the potent anti-SRS-A (leukotriene) activities. These compounds are considered to be of a prophylactic and/or therapeutic value in allergic diseases, such as bronchial asthma, allergic rhinitis and urticaria.

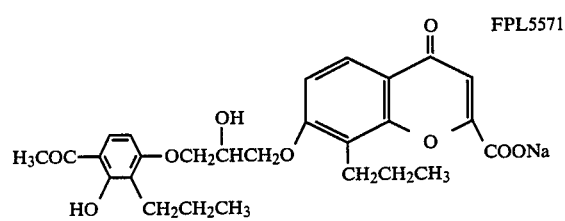

FPL55712

TABLE 2

| No. of example | Inhibitive action of anaphylactic bronchoconstriction | |
|---|---|---|
| | oral dose (mg/kg) | No. of animals protected/No. of animals used |
| 1 | 20 | 3/3 |
| 4 | 20 | 5/5 |
| 8 | 20 | 2/2 |
| 9 | 20 | 2/2 |

What is claimed is:

1. Compounds having general formula (I)

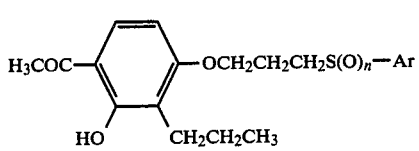

wherein Ar is a pyrazolo[1,5-a]pyridin-3-yl ring which may be substituted by a straight or branched alkyl group having 1 to 4 carbon atoms, or Ar is a benzimidazol-2-yl ring, and n is an integer of 0 to 2, or a pharmaceutically acceptable salt thereof.

2. The compound according to claim 1, which is 2-[3-(4-acetyl-3-hydroxy-2-propylphenoxy)-propylthio]benzimidazole.

3. The compound according to claim 1, which is 3-[3-(4-acetyl-3-hydroxy-2-propylphenoxy)-propylthio]-2-isopropylpyrazolo[1,5-a]pyridine.

4. The compound according to claim 1, which is 3-[3-(4-acetyl-3-hydroxy-2-propylphenoxy)-propylthio]-2-isopropylpyrazolo[1,5-a]pyridine-S-oxide.

5. The compound according to claim 1, which is 3-[3-(4-acetyl-3-hydroxy-2-propylphenoxy)-propylsulfonyl]-2-isopropylpyrazolo[1,5-a]pyridine.

6. The compound according to claim 1, wherein Ar is

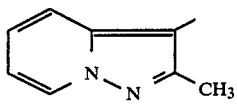

and n is 0.

7. The compound according to claim 1, wherein Ar is

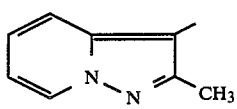

and n is 1.

8. The compound according to claim 1, wherein Ar is

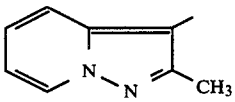

and n is 2.

9. The compound according to claim 1, wherein Ar is

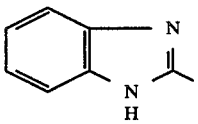

and n is 1.

10. The compound according to claim 1, wherein Ar is

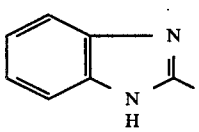

and n is 2.

* * * * *